US00PP16102P2

(12) United States Plant Patent
Brown

(10) Patent No.: US PP16,102 P2
(45) Date of Patent: Nov. 8, 2005

(54) ***ACONITUM* PLANT NAMED 'ROYAL FLUSH'**

(50) Latin Name: *Aconitum carmichaelii*
Varietal Denomination: Royal Flush

(75) Inventor: Bob Brown, Fladburry Pershore (GB)

(73) Assignee: Witteman & Company, Hillegom (NL)

( * ) Notice: Subject to any disclaimer, the term of this patent is extended or adjusted under 35 U.S.C. 154(b) by 22 days.

(21) Appl. No.: 10/945,158

(22) Filed: Sep. 20, 2004

(51) Int. Cl.[7] ..... A01H 5/00
(52) U.S. Cl. ..... Plt./263
(58) Field of Search ..... Plt./263

(56) References Cited

PUBLICATIONS

UPOV 'hit' on 'Royal Flush', UPOV–Rom, GTI Jpuve Retrieval Software, Plant Variety Databases, 2004/06.*

* cited by examiner

*Primary Examiner*—Anne Marie Grunberg
(74) *Attorney, Agent, or Firm*—C. A. Whealy

(57) ABSTRACT

A new and distinct cultivar of *Aconitum* plant named 'Royal Flush', characterized by its upright plant habit; dark green-colored foliage; freely flowering habit; and dark blue-colored flowers.

2 Drawing Sheets

Botanical classification/cultivar designation: *Aconitum carmichaelii* cultivar Royal Flush.

BACKGROUND OF THE INVENTION

The present Invention relates to a new and distinct cultivar of *Aconitum* plant, botanically known as *Aconitum carmichaelii*, and hereinafter referred to by the cultivar name Royal Flush.

The new *Aconitum* is a product of a planned breeding program conducted by the Inventor in Evesham, United Kingdom. The new *Aconitum* originated from a cross-pollination made by the Inventor of an unnamed selection of *Aconitum carmichaelii*, not patented, as the female, or seed, parent and the *Aconitum carmichaelii* cultivar Barker's Variety, not patented, as the male, or pollen, parent. The new *Aconitum* was discovered and selected by the Inventor in 1996 in a controlled environment in Evesham, United Kingdom within the resultant progeny of the stated cross-pollination.

Asexual reproduction of the new cultivar by divisions in Evesham, United Kingdom since 1998, has shown that the unique features of this new *Aconitum* are stable and reproduced true to type in successive generations.

SUMMARY OF THE INVENTION

Plants of the cultivar Royal Flush have not been observed under all possible environmental conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Royal Flush'. These characteristics in combination distinguish 'Royal Flush' as a new and distinct cultivar:

1. Upright plant habit.
2. Dark green-colored foliage.
3. Freely flowering habit.
4. Dark blue-colored flowers.

Compared to plants of the female parent selection, the male parent, the cultivar Barker's Variety, and other selections of *Aconitum carmichaelii* known to the Inventor, plants of the new *Aconitum* are shorter and have a brighter, less faded, blue flower color.

BRIEF DESCRIPTION OF THE PHOTOGRAPHS

The accompanying colored photographs illustrate the overall appearance of the new *Aconitum*, showing the colors as true as it is reasonably possible to obtain in colored reproductions of this type. Colors in the photographs may differ slightly from the color values cited in the detailed botanical description which accurately describe the actual colors of the new *Aconitum*.

The photograph on the first sheet comprises a side perspective view of a typical flowering plant of 'Royal Flush' grown in an outdoor nursery.

The photograph at the top of the second sheet is a close-up view of typical leaves of 'Royal Flush'.

The photograph at the bottom of the second sheet is a close-up view of a typical inflorescence of 'Royal Flush'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following description were about one year-old and grown in an outdoor nursery in Hillegom, The Netherlands during the late summer and early fall. During the production of the plants, day temperatures ranged from 18 to 30° C. and night temperatures ranged from 7 to 18° C.

Botanical classification: *Aconitum carmichaelii* cultivar Royal Flush.

Parentage:

*Female, or seed, parent.*—Unnamed selection of *Aconitum carmichaelii*, not patented.

*Male, or pollen, parent.*—*Aconitum carmichaelii* cultivar Barker's Variety, not patented.

Propagation:

*Type cutting.*—By divisions.

*Rooting time.*—From divisions, it takes about 40 days at 6° C. to produce a rooted young plant.

*Root description.*—Fibrous, freely branching, dense; rust brown in color. Tuber formation has not been observed.

Plant description:

*Form.*—Upright perennial flowering plant with deeply dissected leaves; dark blue-colored galeate flowers arranged on erect racemes.

*Plant height.*—About 70 cm.

*Plant diameter.*—About 21 cm.

*Vigor.*—Moderately vigorous.

*Stem description.*—Internode length: About 4 cm. Shape: Rounded to slightly flattened. Strength: Strong. Texture: Smooth, glabrous. Color: 166A to 187A with tints of green, 143B.

*Foliage description.*—Leaves alternate, simple, generally symmetrical, deeply dissected and long-persisitng. Length: About 14.6 cm. Width: About 15.2 cm. Shape: Deeply dissected, pedately lobed. Apex: Acute. Base: Hastate. Margin: Deeply serrate. Texture, upper surface: Sparsely pubescent. Texture, lower surface: Mostly glabrous; margins, sparsely pubescent. Venation: Palmate. Petiole: Length: About 4.1 cm. Diameter: About 4 mm. Color, upper surface: Between 137A and 139A; venation, between 137A and 139A. Color, lower surface: 138A to 138B; venation, 144A. Petiole color, upper surface: 166A to 187A. Petiole color, lower surface: 143A to 144A.

Flower description:

*Appearance.*—Numerous, single galeate, flowers arranged in terminal racemes; zygomorphic. Flowers not persistent. Flowers face outwardly.

*Quantity of flowers.*—Freely flowering. One primary flowering stem and typically three secondary flowering stems develop during the flowering season; about 15 flowers per primary flowering stem and about eight flowers per secondary flowering stem.

*Natural flowering season.*—Summer to early fall; in the Netherlands; flowering continuous.

*Fragrance.*—Not fragrant.

*Flower longevity on the plant.*—About eight days.

*Inflorescence height.*—About 20 cm.

*Inflorescence diameter.*—About 8.8 cm.

*Flower size.*—Height: About 4.7 cm. Width: About 2.7 cm. Depth: About 3.3 cm.

*Flower buds.*—Length: About 2.9 cm. Diameter: About 1.2 cm. Shape: Ovate. Color: N92A.

*Sepals.*—Appearance/arrangement: Five per flower, petaloid; one upper sepal, two lateral sepals and two lower sepals. Length: Upper sepal: About 3 cm. Lateral sepals: About 2.6 cm. Lower sepals: About 2.4 cm, Width: Upper sepal: About 2 cm. Lateral sepals: About 2.8 cm. Lower sepals: About 2 cm. Shape: Upper sepal: Galeate; apex, rounded to obtuse; base, broadly cuneate. Lateral sepals: Reniform; apex, rounded to obtuse; base, broadly cuneate. Lower sepals: Broadly elliptic; apex, rounded to obtuse; base, broadly cuneate. Margin: Entire. Texture, upper and lower surfaces: Sparsely pubescence. Color: When opening, upper surface: N88B; venation, N88A; towards the base, 144C to 144D. When opening, lower surface: N88A; venation, N89A. Fully opened, upper surface: N88A; venation, N88A. Fully opened, lower surface: N89A; venation, N89A.

*Petals.*—Quantity per inflorescence: Six. Length: About 1.7 cm. Width: Towards the apex, about 4 mm; towards the base, about 2 mm. Shape: Narrowly flabellate to narrowly spatulate. Apex: Emarginate. Base: Cuneate. Margin: Entire. Texture, upper and lower surfaces: Smooth; margins sparsely pubescent. Color, upper and lower surfaces: N88A to N88B.

*Peduncles.*—Length: About 18.5 cm. Diameter: About 4 mm. Aspect: Upright. Strength: Strong. Texture: Sparsely pubescent. Color: 137A to 137B.

*Pedicel.*—Length: About 6 cm. Diameter: About 2 mm. Aspect: About 30° from vertical. Texture: Sparsely pubescent. Color, upper surface: 143A slightly tinted with N200A. Color, lower surface: 143A.

*Reproductive organs.*—Stamens: Quantity: About 50. Filament length: About 1.2 cm. Filament color: Close to 155D; towards the anther, 116D. Anther shape: Broadly oblong; basifixed. Anther length: About 1.2 mm. Anther color: 200A. Pollen amount: Scarce. Pollen color: 159B. Pistils: Quantity: About five. Pistil length: About 1.1 cm. Style length: About 1 cm. Style color: 144A. Stigma shape: Pointed. Stigma color: 144B. Ovary color: 144A.

*Seed/fruit description.*—Seed and fruit development has not been observed.

Disease & pest resistance: Plants of the new *Aconitum* have not been noted to be resistant to pathogens common to *Aconitum.*

Temperature tolerance: Plants of the new *Aconitum* have been observed to tolerate high temperatures of 35° C. and to be hardy to USDA Zone 3.

It is claimed:

1. A new and distinct cultivar of *Aconitum* plant named 'Royal Flush', as illustrated and described.

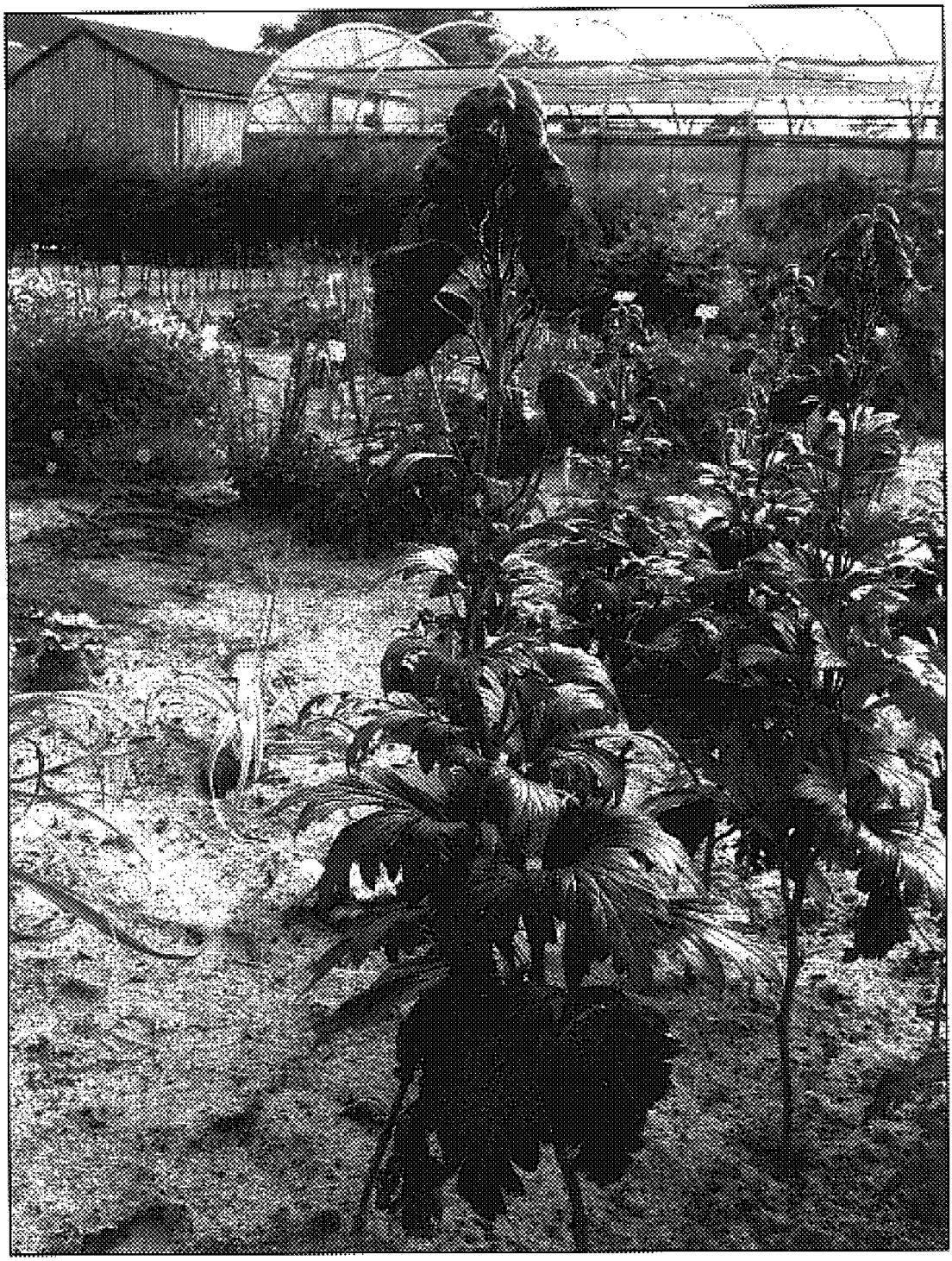

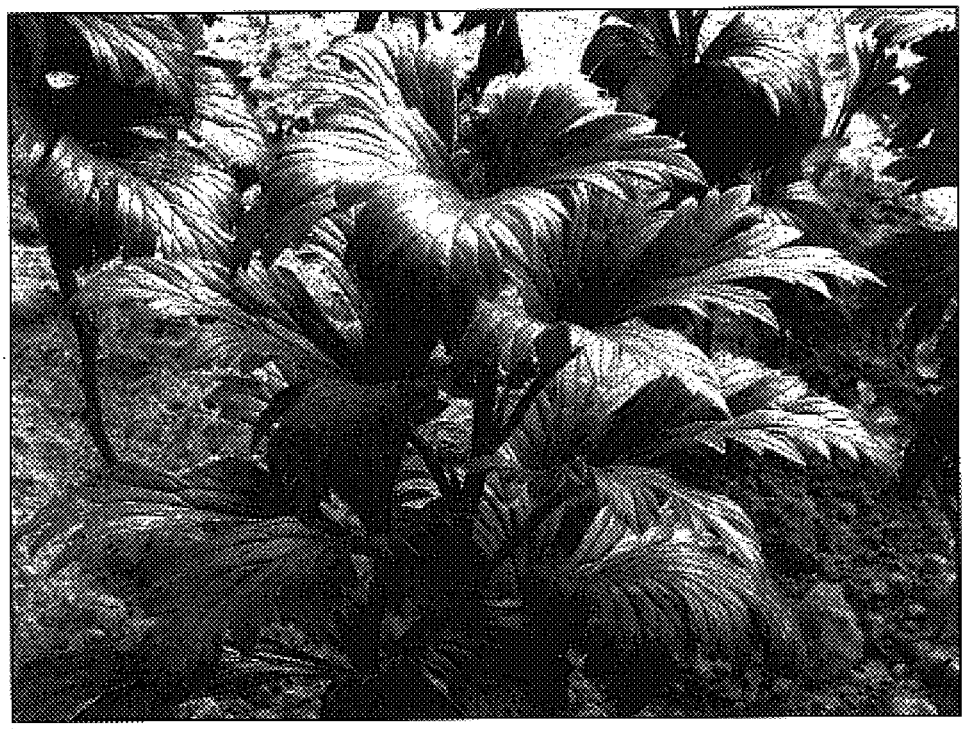
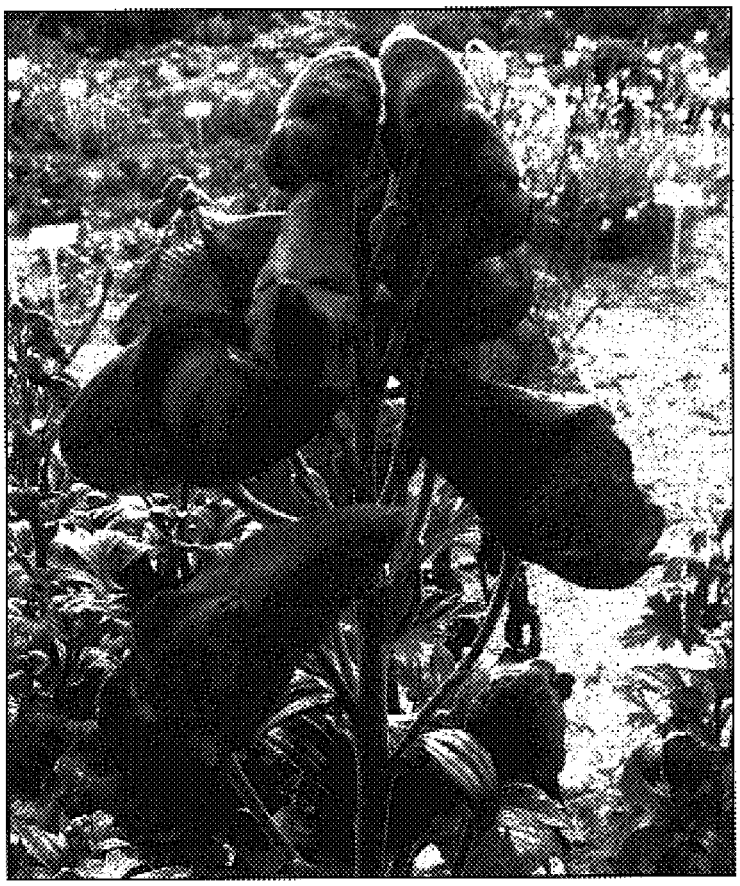

* * * * *